United States Patent [19]
Ding et al.

[11] Patent Number: 5,981,607
[45] Date of Patent: Nov. 9, 1999

[54] EMULSION EYE DROP FOR ALLEVIATION OF DRY EYE RELATED SYMPTOMS IN DRY EYE PATIENTS AND/OR CONTACT LENS WEARERS

[75] Inventors: Shulin Ding, Irvine; Orest Olejnik, Trabuco Canyon; Brenda L. Reis, Costa Mesa, all of Calif.

[73] Assignee: Allergan, Irvine, Calif.

[21] Appl. No.: 09/008,924

[22] Filed: Jan. 20, 1998

[51] Int. Cl.⁶ .......................... A61K 47/12; A61K 47/14; A61K 47/34
[52] U.S. Cl. .......................... 514/785; 514/786; 514/912; 514/915; 514/941; 514/943; 514/975
[58] Field of Search .................................. 514/9, 11, 178, 514/179, 180, 181, 420, 625, 627, 784, 785, 786, 912, 913, 914, 915, 941, 943, 975

[56] References Cited

U.S. PATENT DOCUMENTS

| | | | |
|---|---|---|---|
| 4,839,342 | 6/1989 | Kaswan | 514/11 |
| 5,411,952 | 5/1995 | Kaswan | 514/11 |
| 5,474,979 | 12/1995 | Ding et al. | 514/11 |

FOREIGN PATENT DOCUMENTS

| | | |
|---|---|---|
| 2228198 | 8/1990 | United Kingdom . |
| 95/31211 | 11/1995 | WIPO . |

OTHER PUBLICATIONS

Diagnosis and Management of Tear Film Dysfunction; Stultng & Waring, pp. 445–468 (not dated).
Diagnosis and Management of Dry Eye and Ucular Surface Disorders: OPH Clinic of N.A. vol. 3, No. 4, pp. 575–594, Dec. 1990.

*Primary Examiner*—Jeffrey E. Russel
*Attorney, Agent, or Firm*—Walter A. Hackler

[57] ABSTRACT

An eye drop composition for alleviation of dry eye related symptoms in dry eye patients and contact lens wearers includes an emulsion of a higher fatty acid glyceride, polysorbate 80 and an emulsion stabilizing amount of Pemulen® in water suitable for topical application to ocular tissue.

4 Claims, 7 Drawing Sheets

EMULSION EYE DROP FOR ALLEVIATION OF DRY EYE RELATED SYMPTOMS IN DRY EYE PATIENTS AND/OR CONTACT LENS WEARERS

The present application is related to pending International Patent Application Ser. No. PCT/US95/06302 filed May 17, 1995, designating the United States, which is a continuation-in-part of U.S. patent application Ser. No. 08/243,279 filed May 17, 1994, now U.S. Pat. No. 5,474, 979. The referenced applications/patent are to be incorporated herein by this specific reference thereto.

The present invention relates to a pharmaceutical composition for alleviating dry eye related symptoms, for example, as in patients having immune mediated keratoconjunctivitis sicca (KCS) or dry eye disease or other autoimmune dysfunction of the lacrimal gland, as well as dry eye symptoms of contact lens wearers.

Dry eye generally refers to any tear film abnormality, usually with epithelial abnormalities. A specific deficiency of the aqueous component of the tear film is known as keratoconjunctivitis sicca (KCS), which affects about 30 million people worldwide. It is usually included as part of Sjogren's syndrome. Literally the term denotes inflammation of the cornea and conjunctiva secondary to drying.

When the tear film fails to perform its functions of lubrication, oxygenation, and removal of debris, symptoms of foreign body sensation (grittiness, scratchiness, sandiness), fatigue, and dryness result. A patient may experience severe pain, especially in the presence of filamentary keratopathy. Loss of the smooth refractive surface of the tear film causes blurred vision, which can vary from blink to blink, accounting for a variable manifest refraction and for complaints of variable vision throughout the day. Surface drying may produce reflex tearing and the misleading complaint of excess tears. Typically, symptoms of tear deficiency are worse late in the day, with prolonged use of the eyes (as when the patient reads or watches television), and in conditions of heat, wind, and low humidity (as on the beach or ski slopes). Symptoms that are worse in the morning suggest an associated chronic blepharitis, recurrent corneal epithelial erosion, or exposure keratopathy. Further, symptoms include superficial punctate erosions, corneal filaments, coarse mucus plaques, and epithelial defects.

As hereinabove noted, most of these symptoms result from the unstable tear film and abnormal ocular surface that diminish the ability of the ocular surface to respond to environmental challenges. Dry eye syndrome, if left untreated, can cause progressive pathological changes in the conjunctival and corneal epithelium.

The etiologies of dry eye are varied. The disease generally referred to as "dry eye" may be the result of age-related decreases in systemic androgen support to the lacrimal gland or systemic autoimmune diseases such as Sjogrens Syndrome. A growing body of research suggests that dry eye is the result of an underlying cytokine and receptor-mediated inflammatory process.

Palliative agents, such as tear replacement, tear preservation, and autonomic tear stimulation, may provide complete or partial relief of symptoms. However, therapeutic treatments directed at the underlying inflammatory process may prove beneficial in correcting the underlying disorder.

The tear film in a normal eye consists of a thin (about 6–45 um in thickness) film composed of a mucous layer lying over the corneal epithelium and an aqueous layer covering the mucous layer and epithelium, which is in turn covered by an extremely thin (0.01–0.22 um) layer of lipid molecules.

The presence of a continuous tear film is important for the well-being of the corneal and conjunctival epithelium and provides the cornea with an optically high quality surface. In addition, the aqueous part of the tear film acts as a lubricant to the eyelids during blinking of the lids. Furthermore, certain enzymes contained in the tear fluid, for example, immunoglobulin A, lysozyme and beta lysin, are known to have bacteriostatic properties.

It is believed that the lipid layer is responsible for retarding evaporation of water from the eye. If the lipid layer of the tear film is disturbed by, for example, trauma, disease, irritation of the eye or contact lens wear, excessive evaporation of water from the eye may occur, leaving the surface of the eye "dry" (see e.g., Cedarstaff and Tomlinson, Am. J. Optometry & Physiol. Optics, 60:167–174, 1983 [tear film disruption in patients with keratoconjunctivitis sicca, or "dry eye"]).

A normal lacrimal system functions to form and maintain a properly structured, continuous tear film. The lacrimal system consists of the secretory system (the source), the distribution system and the excretory system (the sink). In the secretory system, aqueous tears are supplied by the main and accessory lacrimal glands.

Excessive evaporation of water from the tear film results in ocular discomfort (frequently experienced by the person as dryness or tired eyes or other less frequently reported discomfort symptoms) and may eventually lead to physiological and pathological changes in the tissue of the eye, especially in the cornea. For contact lens wearers, such discomfort is particularly acute because the loss of water from the tear film occurs at the interface between the tear film and the lens. Further, if the lens is a hydrogel "soft" lens, excessive evaporation of water from the tear film can also result in excessive evaporation of water from the lens.

Thus taking into account this evaporation, the continuous production and drainage of aqueous tear is important to maintaining the corneal and conjunctival epithelium in a moist state, in providing nutrients for epithelian respiration, in supplying bacteriostatic agents and in cleaning the ocular surface by the flushing action of tear movement.

Abnormalities of the tear film include an absolute or partial deficiency in aqueous tear production (keratoconjunctivitis sicca or KCS).

In relatively mild cases, the main symptom of KCS is a foreign body sensation or a mild "scratchiness". This can progress to become a constant, intense burning irritative sensation which can be debilitating to the patient.

More severe forms of KCS progress to the development of filamentary keratitis, a painful condition characterized by the appearance of numerous strands or filaments attached to the corneal surface. Recent evidence suggests that these filaments represent breaks in the continuity of the normal corneal epithelial cells. The shear created by lid motion pulls these filaments, causing pain. Management of this stage of KCS is very difficult.

A frequent complication of KCS is secondary infection. Several breakdowns in the eye's normal defense mechanism seem to occur, presumably attributable to a decrease in the concentration of antibacterial lysozyme in the aqueous tears of a patient suffering from KCS.

Normally, aqueous-deficient dry eye states, such as, for example, KCS, are treated by supplementation of the tears with artificial tear substitutes. However, relief is limited by the retention time of the administered artificial tear solution in the eye. Typically, the effect of an artificial tear solution administered to the eye dissipates within about thirty to forty-five minutes. The effect of such products, while soothing initially, does not last long enough. The patient is inconvenienced by the necessity of repeated administration of the artificial tear solution in the eye as needed to supplement the normal tears.

Presently, artificial tear preparations, lens rewetting solutions and ophthalmic lubricants and ointments utilizing active components other than monolayer forming long chain fatty alcohols are extant in the art. Such available artificial tear solutions commonly include carboxymethyl, methyl or ethyl cellulose or polyvinyl alcohol as the principal active ingredient. Lubricants and ointments tend more toward replacement of oil in the lipid layer of the tear film and commonly include petrolatum, lanolin and/or mineral oil. Contact lens rewetting products vary in composition to a greater extent; however, the solutions are typically aqueous, buffered solutions which frequently contain carboxymethyl, methyl or ethyl cellulose, polyvinyl alcohol and/or glycerin.

Recently, several lecithin and phospholipid-based solutions have been proposed as treatments to reduce evaporation of water from the tear film. U.S. Pat. No. 4,421,748, to Trager, issued Dec. 20, 1983, discloses an artificial tear composition comprising an aqueous hypotonic solution of lecithin and a viscosity adjusting agent for the alleviation of dry eye conditions.

U.S. Pat. No. 5,474,979, hereinabove referenced and incorporated herein by reference thereto, teaches novel pharmaceutical compositions incorporating chemicals which are poorly soluble in water and is more particularly related to a novel ophthalmic emulsion including cyclosporin in admixture with castor oil and polysorbate 80 with high comfort level and low irritation potential.

The present invention is directed to an emulsion system which utilizes higher fatty acid glycerides but in combination with polysorbate 80 which results in an emulsion with a high comfort level and low irritation potential suitable for delivery of medications to sensitive areas such as ocular tissues as well as being suitable itself for alleviating dry eye symptoms.

SUMMARY OF THE INVENTION

In accordance with the present invention, a non-irritating pharmaceutical composition with high comfort level and low irritation potential suitable for delivery to sensitive areas such as ocular tissues comprises an admixture of an emulsifying amount of a higher fatty acid glycerol and polysorbate 80. The higher fatty acid glyceride may comprise, for example, castor oil, corn oil, sunflower oil or light mineral oil. The emulsion may also be used to advantage for introducing an active agent such as cyclosporine as set forth in parent U.S. Pat. No. 5,474,979. In one embodiment, the composition may comprise an active agent such as, for example, cyclosporine.

Preferably, the weight ratio of the castor oil to the polysorbate 80 is between about 0.3 to about 30 and a weight ratio of the active agent to the fatty acid glyceride is below 0.16. More preferably, the weight ratio of castor oil to polysorbate 80 is between 0.5 and 12.5, and the weight ratio of active agent to castor oil is between about 0.001 to about 0.7.

When an active agent is dissolved in the oil phase in accordance with the present invention, the emulsion is found to be physically stable upon long term storage. No demulsification or crystallization of active agent was noticed after up to one year at room temperature.

Most importantly, the emulsion of the present invention provides for long retention of the higher fatty acid glyceride when the emulsion is instilled into an eye. This in turn can retard water evaporation from the eye which alleviates dry eye symptoms.

BRIEF DESCRIPTION OF THE DRAWINGS

The advantages and features of the present invention will be better understood by the following description when considered in conjunction with the accompanying drawings, in which.

DETAILED DESCRIPTION

An ocular monolayer with significant efficiency of water evaporation retardation should spread effectively and form a compressed film after spreading has occurred. Furthermore, the compressed film should be sufficiently flexible so that when broken by wind, the eye lids or a contact lens, it will re-form promptly, and, therefore, reduce the tear film local dryup and breakup.

The discovery on which the present invention is founded relates to an emulsion of a higher fatty acid glyceride such as, for example, castor oil, corn oil, sunflower oil or light mineral oil and an emulsifier and dispersing agent, polysorbate 80. The selection of these components could not have been anticipated on the basis of conventional thinking.

Polysorbate 80 is a mixture of oleate esters of sorbitol and sorbitol anhydrides, consisting predominantly of the monoester, condensed with approximately 20 moles of ethylene oxide. It conforms generally to the formula:

where w+x+y+z has an average value of 20. Polysorbate 80 is available from ICI Americas, Inc., Wilmington, Del.

For example, it is well known that castor oil is irritating to sensitive tissues such as the eye. Thus, conventional teaching in the art is away from a formulation which utilizes a higher fatty acid glyceride, such as castor oil, by itself or in combination with an active agent.

Other than U.S. Pat. No. 5,474,979 hereinabove referenced and incorporated herein by reference thereto, there are no examples of polysorbate 80 in combination with castor oil which produces an emulsion with a high comfort level and low irritation potential suitable for the delivery of medication to sensitive areas such as ocular tissues.

In accordance with the present invention, the emulsions can be further stabilized using a polyelectrolyte, or polyelectrolytes if more than one, from the family of cross-linked polyacrylates, such as carbomers and Pemulen®.

Pemulen® is a polymeric emulsifier having a CTFA name of Acrylates/C10-30 Alkyl Acrylate Cross-Polymer and is described in the "Carbomer 1342" monograph in the USPXXII/NFXVII.

Carbomer 1342 is a high molecular weight copolymer of acrylic acid and a long chain alkyl methacrylate cross-linked with allyl ethers of pentaerythritol. Carbomer 1342, previously dried in vacuum at 80° for 1 hour, contains not less than 52.0 percent and not more than 62.0 percent of carboxylic acid (—COOH) groups. The viscosity of a neutralized 1.0 percent aqueous dispersion of Carbomer 1342 is between 9,500 and 26,500 centipoises.

Carbomer 1342 is available from B. F. Goodrich. Carbomer 1382 is also available from B. F. Goodrich in a high molecular weight copolymer of acrylic acid and a long chain alkyl methacrylate cross-linked with allyl ethers of pentaerythritol.

In addition, the tonicity of the emulsions can be further adjusted using glycerine, mannitol, or sorbitol if desired. The pH of the emulsions can be adjusted in a conventional manner using sodium hydroxide to a near physiological pH level and while buffering agents are not required, suitable buffers may include phosphates, citrates, acetates and borates.

While a medication in accordance with the present invention may include cyclosporine, other chemicals which are poorly soluble in water such as indomethacin and steroids such as androgens, prednisolone, prednisolone acetate, fluorometholone, and dexamethasones, may be emulsified with castor oil and polysorbate 80 resulting in a composition with similar low irritation potential.

Figure 1:
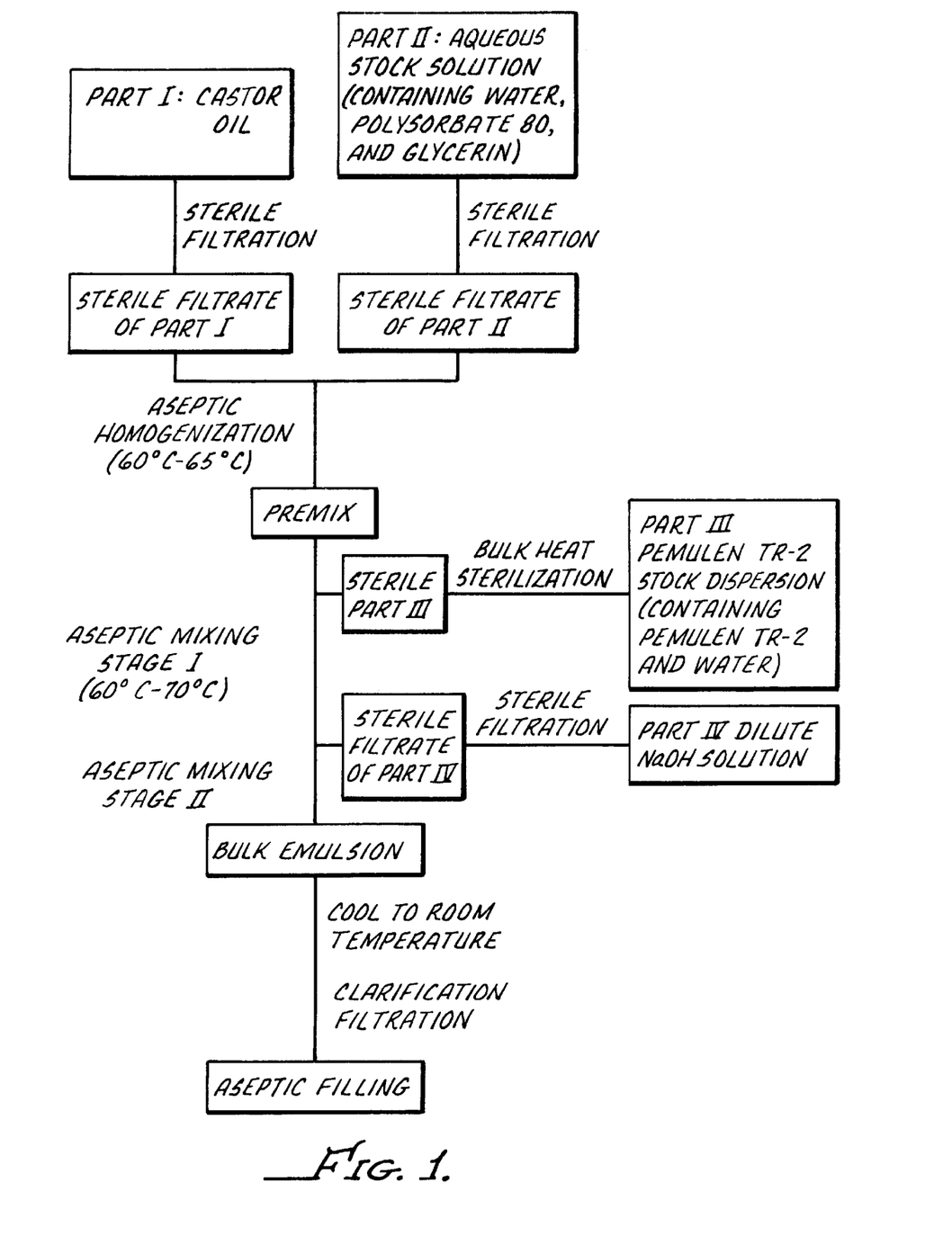
FIG. 1 is a manufacturing schematic for production of sterile emulsion in accordance with the present invention.

The invention is further illustrated by the following examples with all parts and percentages expressed by weight. Emulsions were prepared according to the manufacturer's schematic shown in FIG. 1.

EXAMPLE 1

|  | A | B | C | D |
|---|---|---|---|---|
| Castor oil | 5.00% | 2.50% | 1.25% | 0.625% |
| Polysorbate 80 | 1.00% | 1.00% | 1.00% | 1.00% |
| Pemulen ® | 0.05% | 0.05% | 0.05% | 0.05% |
| Glycerine | 2.20% | 2.20% | 2.20% | 2.20% |
| NaOH | qs | qs | qs | qs |
| Purified water | qs | qs | qs | qs |
| pH | 7.2–7.6 | 7.2–7.6 | 7.2–7.6 | 7.2–7.6 |

EXAMPLE 2

|  | A |
|---|---|
| Castor oil | 2.50% |
| Polysorbate 80 | 0.75% |
| Carbomer 1382 | 0.05% |
| Glycerine | 2.20% |
| NaOH | qs |
| Purified water | qs |
| pH | 7.2–7.6 |

The formulations set forth in Examples 1–2 were used for treatment of keratoconjunctivitis sicca (dry eye) syndrome with Example 2, Carbomer 1382 replacing the Pemulen®.

It should be appreciated that while specific examples hereinabove are presented for illustration purposes, the range of the fatty acid glyceride, which may be castor oil, corn oil, sunflower oil or light mineral oil, may vary between about 0.5 and about 10 percent by weight. The range of Polysorbate 80 may be between about 0.2 and about 5 percent, by weight, and the range of Pemulen® may be between about 0.05 and about 2 percent, by weight.

The following clinical tests were performed in a double marked randomized study to measure aqueous deficiency in keratoconjunctivitis sicca. These clinical tests include the Schirmer, Rose Bengal Staining and Fluorescein used to determine punctate Keratitis. In addition, subject tests hereinafter presented show a relative assessment based on patient reports of stinging/burning, tearing, discharge, itching, foreign body sensation, blurred vision, dryness, photophobia, and pain.

CLINICAL TESTS

Schirmer

Clinical measures of tear film volume and tear flow rates help quantitate the severity of aqueous deficiency in keratoconjunctivitis sicca.

The Schirmer test measures the volume of tears produced during a fixed time period. It is performed by placing the folded 5-mm. end of a standard size number 41 Whatman filter paper strip over the lower lid, between its middle third and lateral third. After 5 minutes the strip is removed, and the amount of wetting is measured from the fold.

Figure 2:
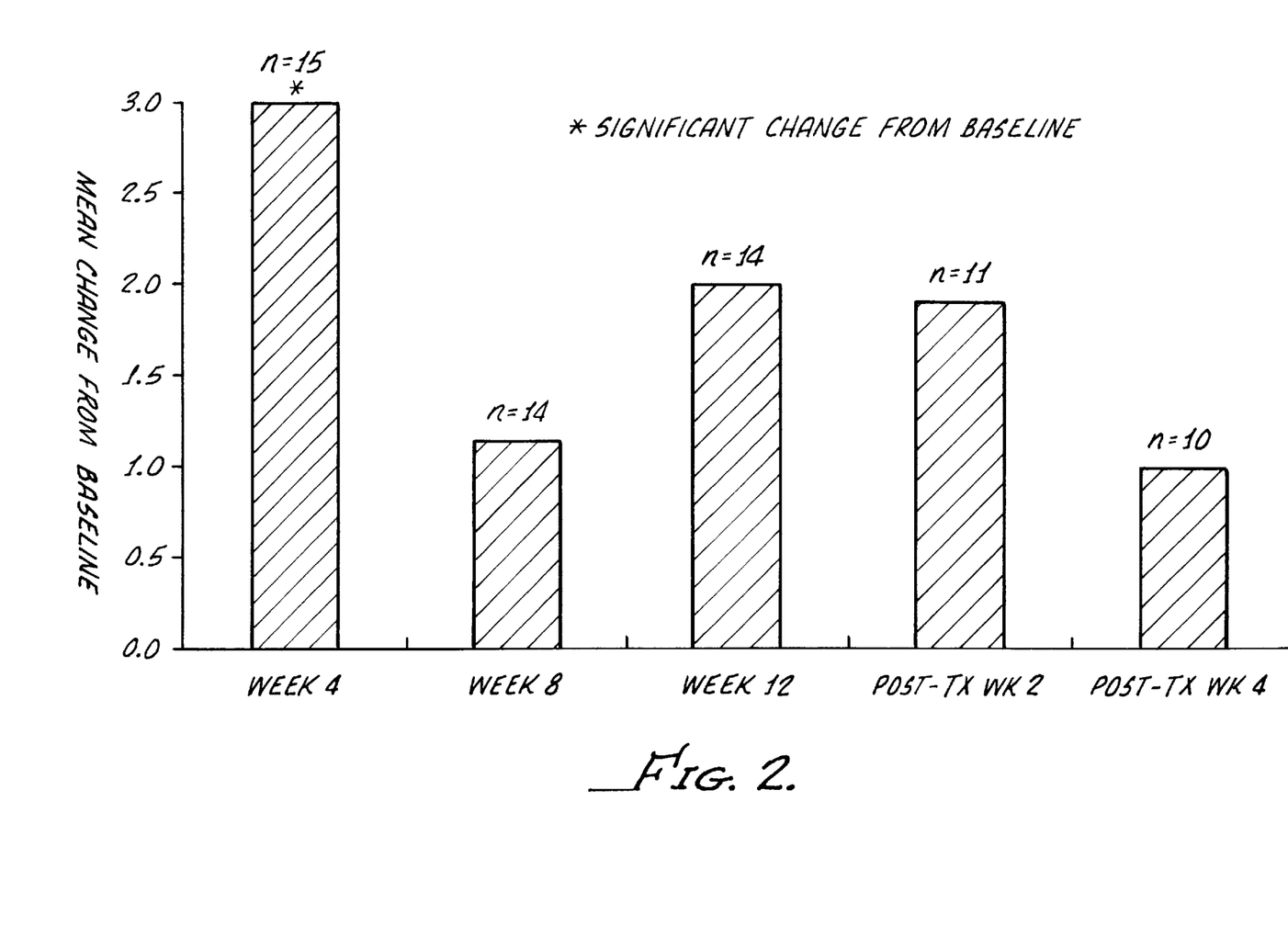
FIG. 2 is a bar graph showing mean change from baseline as a function of time as clinically diagnosed using the Schirmer test following the instillation of the emulsion in accordance with the present invention.

The relative amount of wetting as a function of time following instillation of the emulsion of Example 1B into an eye of a patient, is shown in FIG. 2, the number of patients being indicated on the bar graph by the character "n". As shown, the instillation of the emulsion increases the measured tear volume.

Rose Bengal Staining

As hereinabove discussed, patients with tear film dysfunction may become symptomatic because of dry spots on the cornea. Identification of dry areas with topically applied stains substantiates the diagnosis. Patients who complain of nonspecific itching, burning, and stinging without identifiable corneal surface pathology present a more difficult diagnostic problem. The two commonly used dyes are rose bengal and fluorescein.

Rose bengal is a red aniline dye related to fluorescein that stains devitalized and degenerating corneal and conjunctival cells, mucus, and filaments. A full drop of a 1% solution may elicit pain. Placing a drop on the wooden end of a cotton tip applicator and then touching it to the eye will reduce the volume delivered to approximately one third of a drop. A micropipette (Pipetteman, Ranin, Woburn, Mass.) may be used to deliver 2.5 uL to 5.0 uL into the inferior fornix. This standardizes the amount, is sufficient to obtain adequate staining, and is not uncomfortable to the patient. Using the green filter, a score is given to each medial and lateral interpalpebral zones.

Figure 3:
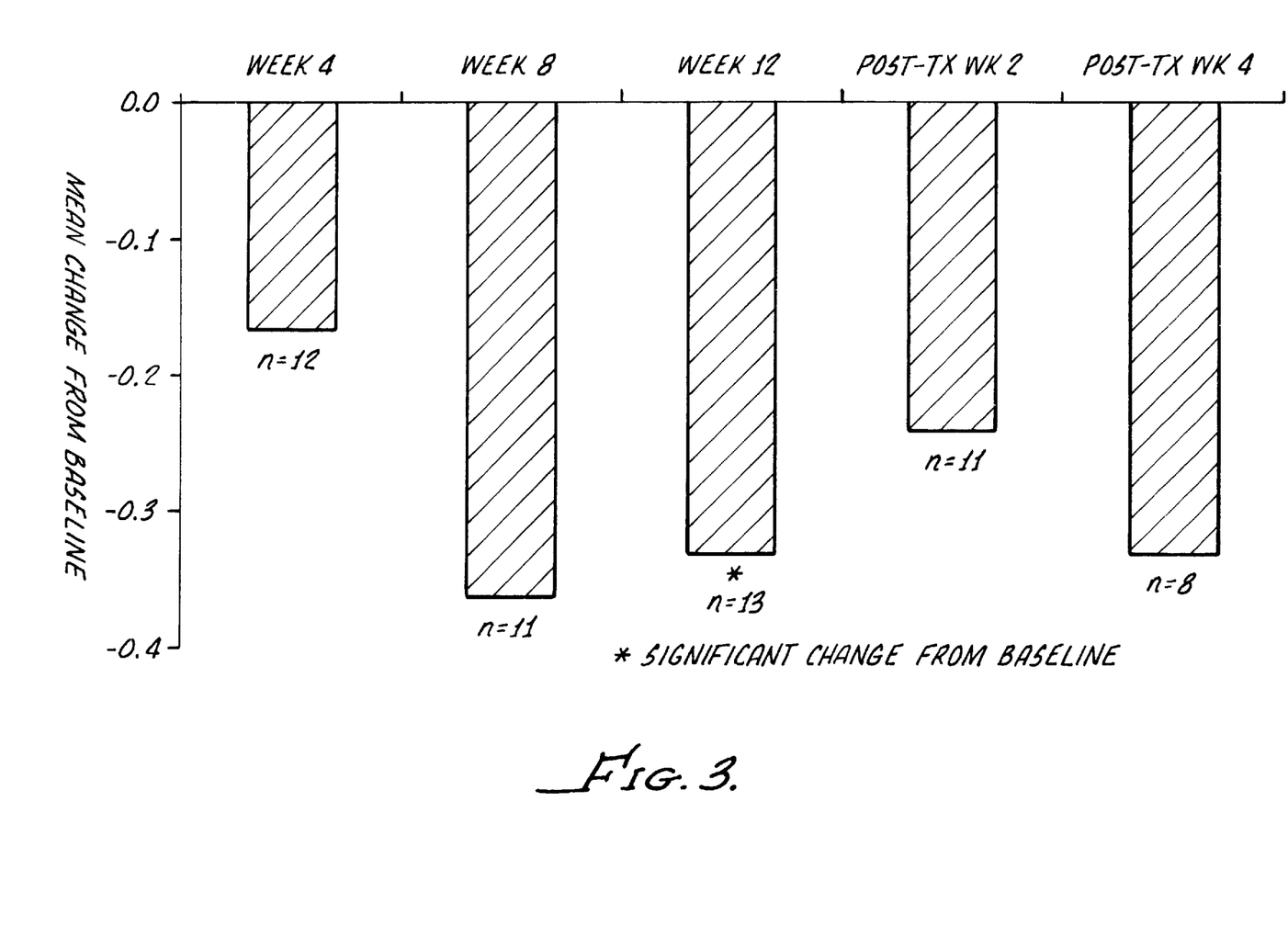
FIG. 3 is a bar graph showing mean change from baseline as a function of time as clinically diagnosed using the Temporal Rose Bengal Staining test following the instillation of the emulsion in accordance with the present invention.

As shown in FIG. 3, a mean charge in score is shown as a function of time using Temporal Rose Bengal Staining following instillation of the emulsion of Example 1B. These changes represent significant reduction in conjunctival dry areas.

Superficial Punctuate Keratitis

Figure 4:
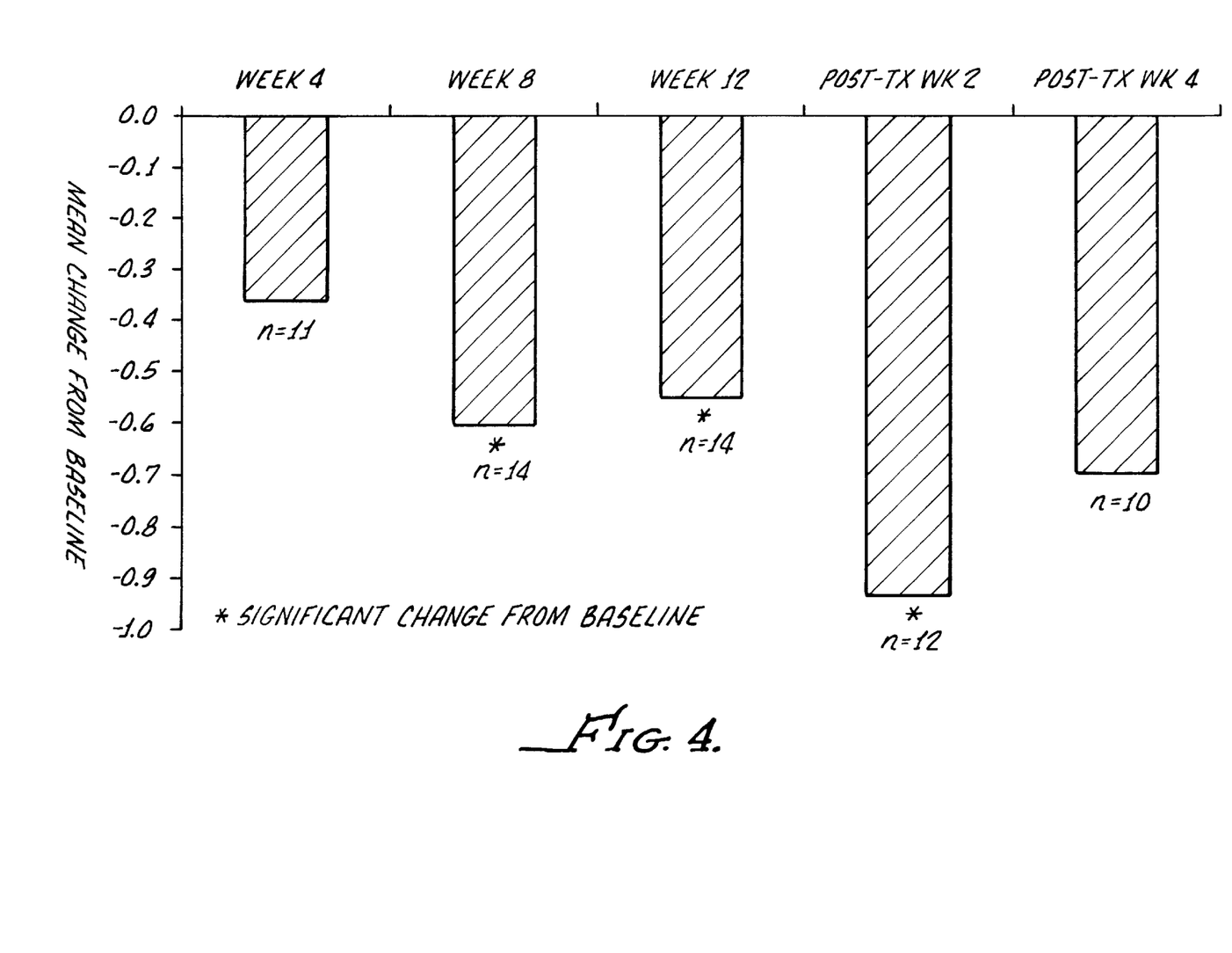
FIG. 4 is a bar graph showing change in superficial punctate Keratitis, as measured with fluorescein, as a function of time following the instillation of the emulsion in accordance with the present invention.

Fluorescein is used to determine punctate Keratitis. Fluorescein is also an aniline dye that differs from rose bengal in that it stains areas of epithelial cell loss and not devitalized epithelium. Fluorescein is available in sterile filter paper strips or as a 2% solution, alone or in combination with topic anesthetic. One drop of 2% fluorescein provides an excessive amount of fluorescein. A sterile fluorescein strip touches to the inferior tear lake is preferred. Patterns of conjunctival and corneal staining similar in distribution to rose bengal staining are shown in FIG. 4.

SUBJECTIVE TESTS

Figure 5:
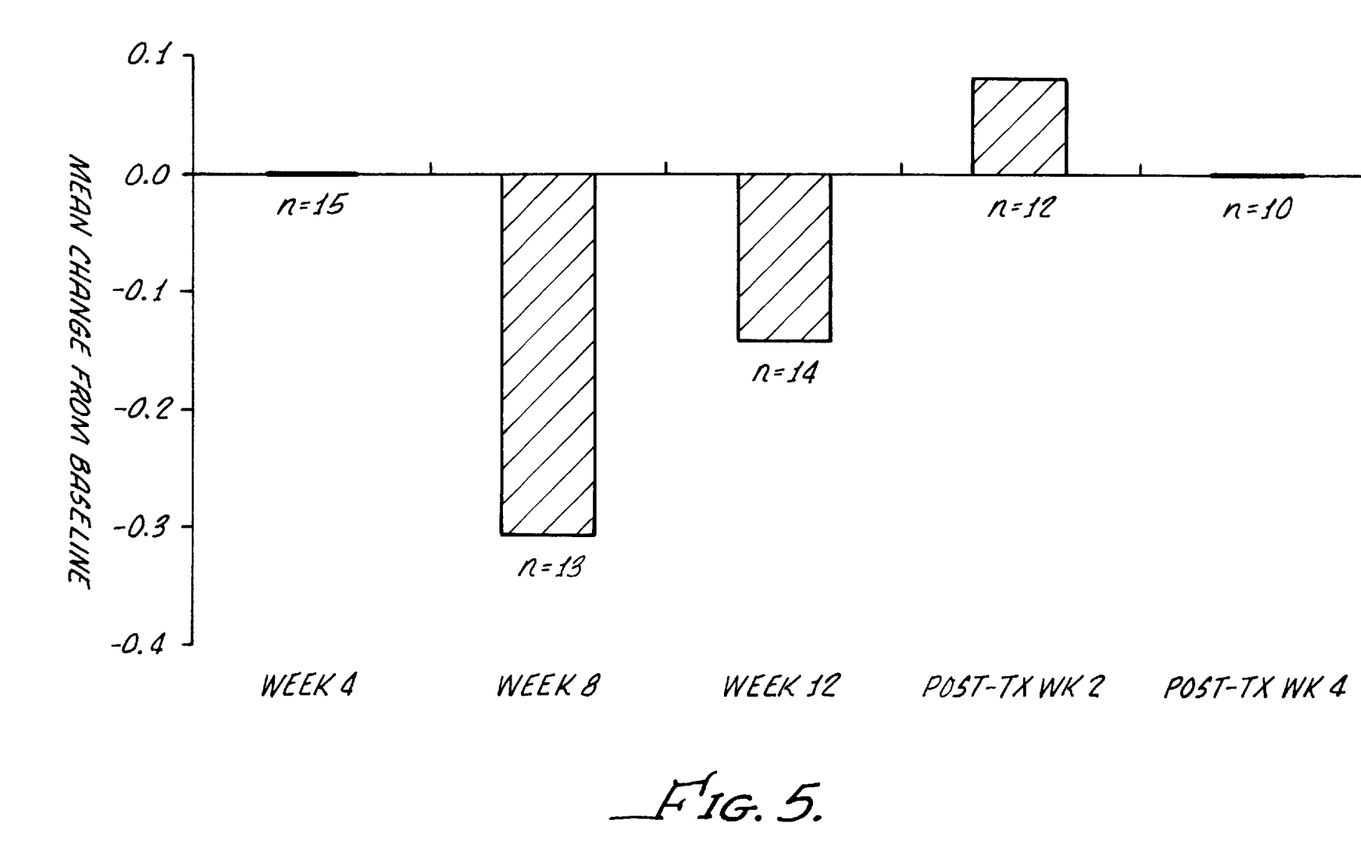
FIG. 5 is a bar graph of subjective reports of Burning and Stinging by patients as a function of time following instillation of the emulsion in accordance with the present invention.
Figure 6:
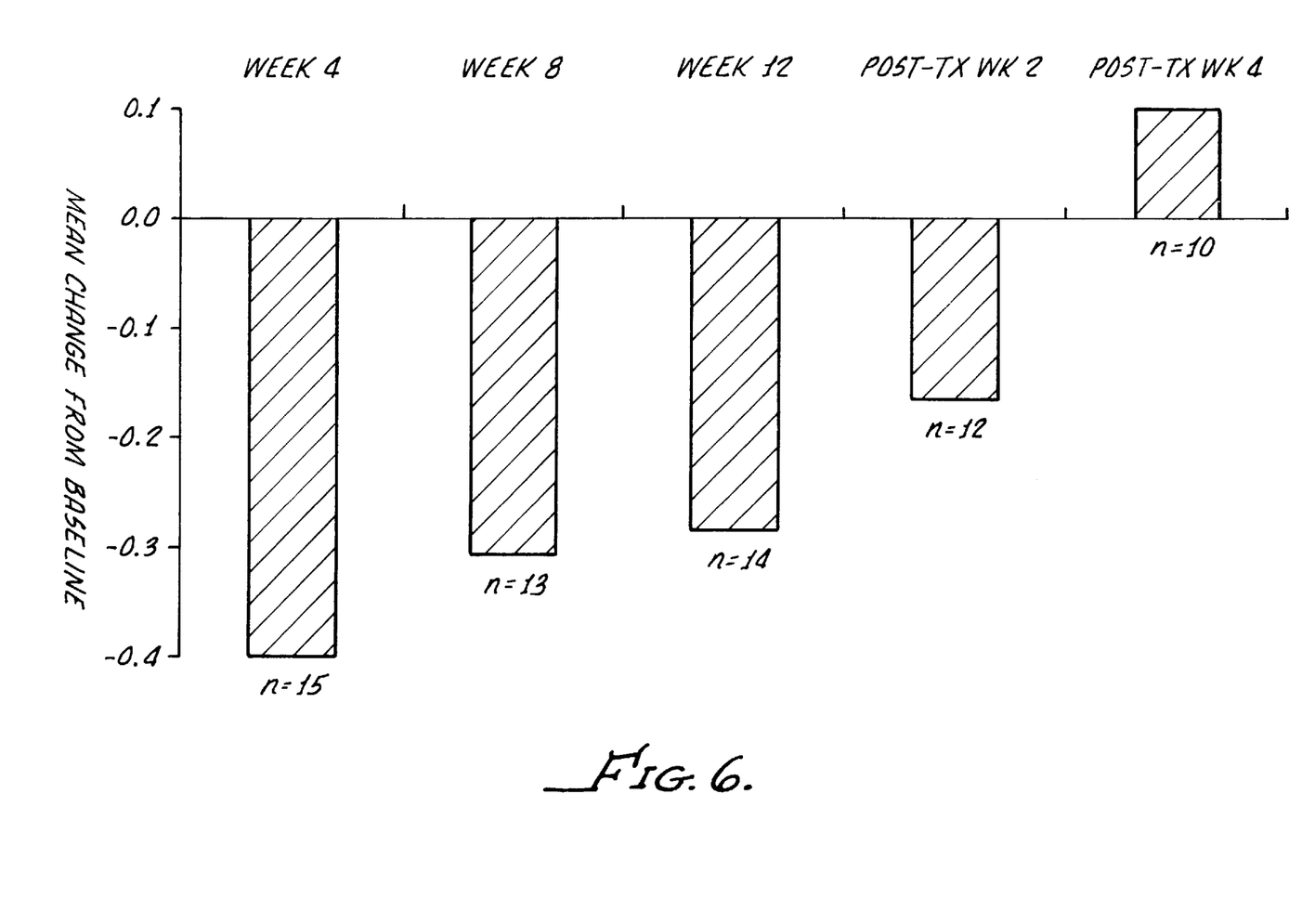
FIG. 6 is a bar graph of subjective reports of Ocular dryness as a function of time following instillation of the emulsion in accordance with the present invention.

Subjective Tests on patients reporting ocular burning/stinging and ocular dryness are shown in FIGS. 5–6.

Subjects responded about symptoms of ocular discomfort for each eye and in a weekly diary, subjects recorded how both eyes felt on average for symptoms of ocular discomfort.

Subjective assessment on several indices: stinging/burning, tearing, discharge (not associated with infection), itching, foreign body sensation, blurred vision, dryness, photophobia, pain and other. Assessment employed a 5 point Liukert Scale where 0=no discomfort, +1=mild, +2=moderate, +3=severe, and +4=very severe.

The grading of symptoms of discomfort for either eye will be defined as follows:

| None | (0) = No discomfort |
| Mild | (+1) = Awareness, but no discomfort and no intervention required. |
| Moderate | (+2) = Discomfort that causes intermittent awareness and requires intervention. |
| Severe | (+3) = Discomfort that causes continuous awareness and requires intervention. |
| Very Severe | (+4) = Discomfort that interferes with normal daily activity and requires intervention. |
| Other | (9) = I do not remember (used only in Subject Diary). |

Tolerability of the emulsion by the subject was evaluated immediately after instillation of masked study medication, then at 15 and 30 minutes post-instillation. Subjective assessment on several indices: stinging/burning, itching, foreign body sensation, blurred vision photophobia, pain and other. Assessment employed a 5 point Likert Scale where 0=no discomfort, +1=mild, +2=moderate, +3=severe, and +4=very severe. Duration of recorded symptoms will also be recorded in seconds only immediately after instillation of masked medication.

The grading of the symptoms of discomfort for either eye will be defined as follows:

| None | (0) = No discomfort. |
| Mild | (+1) = Awareness, but no discomfort. |
| Moderate | (+2) = Discomfort that causes intermittent awareness. |
| Severe | (+3) = Discomfort that causes continuous awareness. |
| Very Severe | (+4) = Discomfort that interferes with normal daily activity. |

The results shown in FIGS. 5–6 reveal that reduction in subject ocular burning/stinging and dryness occur follows instillation of the emulsions of Example 1B.

Retention Time

As can be appreciated, retention of the emulsion in the subject's eye is also important in achieving the objectives of the present invention. In that regard, emulsion in accordance with the present invention can provide a mean ocular residue time of castor oil in ocular tissue for up to about three hours.

This has been established by an interferometric study in Beagle dog eyes, as follows:

General Method

After a baseline examination of the tear film is documented (VHS recorder), one drop of formulation B.C. D. shown in Example 1 and a further formulation having 0.125% w/w of castor oil was instilled superiorly onto the corneal surface of a Beagle dog eye, and a three minute observation time point was carried out (T0–3 min.). Additional observation points are made at 20, 60, 120, and 240 minutes post instillation. The results are shown in FIG. 7.

Figure 7:
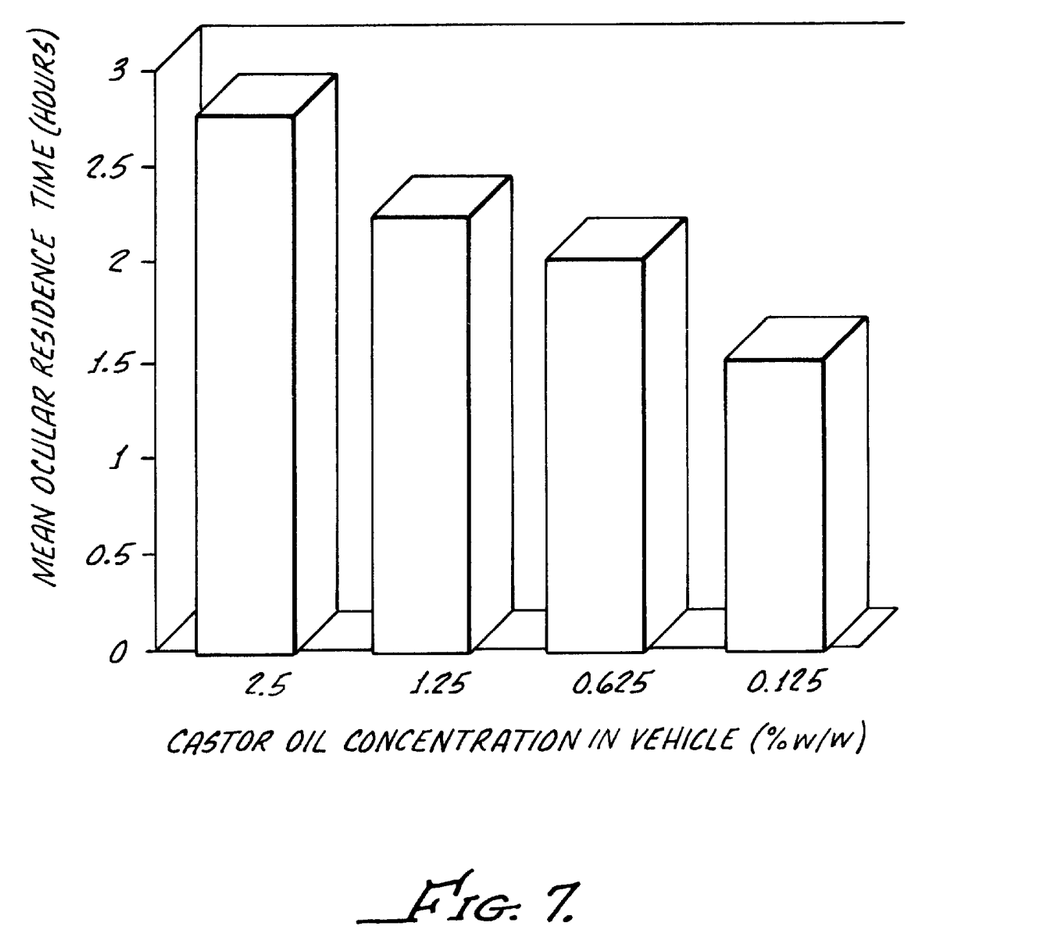
FIG. 7 is a bar graph of mean ocular residue time, in hours, as a function of the amount of fatty acid glyceride in an emulsion in accordance with the present invention.

The results shown in FIG. 7 are based on the Guillon Technique. The primary components for carrying out the tear evaluations are: a Keeler Tearscope, CCD camera and remote, color monitor, VDR and cassettes, and a slit lamp bio-microscope. For observing and recording the tear fringes the tearscope is the most important component, as it is a highly specialized light source.

A semi-quantitative determination (Guillon Technique) of the thickness of the lipid/oil component of the pre-ocular tear film (POTF) was carried out with review of the video film footage of the experiments.

It should be appreciated that castor oil itself will abolish the lipid layer completely. Accordingly, it is unexpected that the emulsions in accordance with the present invention can provide substantial residence time for castor oil in the eye.

Although there has been hereinabove described a particular pharmaceutical composition in the form of a nonirritating emulsion for the purpose of illustrating the manner in which the invention may be used to advantage, it should be appreciated that the invention is not limited thereto. Accordingly, any and al modifications, variations or equivalent arrangements, which may occur to those skilled in the art, should be considered to be within the scope of the present invention as defined in the appended claims.

What is claimed is:

1. A method for alleviation of dry eye related symptoms in dry eye patients and contact lens wearers, said method comprising topically applying to ocular tissue an emulsion of a higher fatty acid glyceride, polysorbate 80 and an emulsion stabilizing amount of Pemulen in water, said emulsion being characterized by an absence of cyclosporin.

2. The method according to claim 1 wherein the weight ratio of the higher fatty acid glyceride to the polysorbate 80 in the emulsion is between about 0.3 and about 30.

3. The method according to claim 2 wherein the higher fatty acid glyceride in the emulsion is selected from the group consisting of castor oil and corn oil.

4. The method according to claim 3 wherein castor oil is present in the emulsion in an amount of between about 0.625%, by weight, and about 5.0%, by weight, the polysorbate 80 is present in an amount of about 1.0%, by weight, the Pemulen is present in an amount of about 0.05%, by weight, and the glycerine is present in an amount of about 2.2%, by weight.

* * * * *